(12) United States Patent
Ahmed et al.

(10) Patent No.: US 7,608,615 B2
(45) Date of Patent: Oct. 27, 2009

(54) PYRROLO[2,1-C][1,4]BENZODIAZEPINE HYBRIDS AND A PROCESS FOR THE PREPARATION THEREOF

(75) Inventors: Kamal Ahmed, Andhra Pradesh (IN); Venkata Ramana Adhi, Andhra Pradesh (IN); Hari Babu Ankati, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 11/893,380

(22) Filed: Aug. 14, 2007

(65) Prior Publication Data

US 2008/0064685 A1    Mar. 13, 2008

(30) Foreign Application Priority Data

Aug. 14, 2006   (IN) .................. 1822/DEL/2006

(51) Int. Cl.
*C07D 403/12* (2006.01)
*A61K 31/5513* (2006.01)
*A61P 35/00* (2006.01)

(52) U.S. Cl. ..................... 514/220; 540/496
(58) Field of Classification Search ................ 540/496; 514/220
See application file for complete search history.

(56) References Cited

OTHER PUBLICATIONS

Gregson et al., "Design, synthesis and evaluation of a novel pyrrolobenzodiaepine DNA-interactive agent with highly efficient cross-linking ability and potent cytotoxicity", *J Med Chem* (2001) 44:737.
Hurley et al., "Pyrrolo(1,4) benzodiazepine antitumor antibiotics. In vitro interaction of anthramycin, sibiromycin and tomaymycin with DNA using specifically radiolabelled molecules", *Biochem Biophys Acta* (1977) 475:521.
Kamal et al., "Design, synthesis and evaluation of new noncrosslinking pyrrolobenzodiazepine dimers with efficient DNA binding ability and potent antitumor activity," *J Med Chem* (2002) 45:4679.
Kamal et al., "A new route to 4-phnyl-2(1H) quinazolinones; reactions of 2-amino benzophenones with chlorosulfonyl isocyanate", *Syn Commun* (1980) 10:799-804.
Kaplan and Hurley, "Anthramycin binding to deoxyribonucleic acid-mitomycin C complexes. Evidence for drug-induced deoxyribonucleic acid conformational change and cooperativity in mitomycin C binding", *Biochemistry* (1981) 20:7572.
Kunimoto et al. "Mazethramycin, a new member of anthramycin group antibiotics", *J Antibiot* (1980) 33:665.
Thurston et al., "Synthesis of a novel GC-specific covalent-binding DNA affinity-cleavage agent based on pyrrolobenzodiazepines (PBDs)," *Chem Commun* (1996) 563-565.
Thurston et al., "Synthesis of Sequence-Selective C8-Linked Pyrrolo[2,1-c] [1,4] benzodiazepine DNA Interstrand Cross-Linking Agents", *J Org Chem* (1996) 61:8141.

*Primary Examiner*—Bruck Kifle
(74) *Attorney, Agent, or Firm*—DLA Piper LLP (US)

(57) ABSTRACT

The present invention provides quinazolinone linked pyrrolo[2,1-c][1,4]benzodiazepine hybrid of general formula 5,

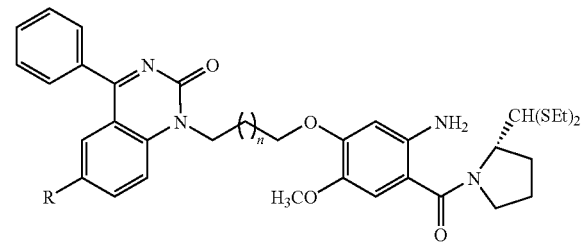

Formula 5 wherein, R is alkyl or halo group selected from H, Cl, F or $CH_3$ and n=1 to 3 useful for antitumour/anticancer activity. The present invention also provides a process for the preparation of quinazolinone linked pyrrolo[2,1-c][1,4]benzodiazepine hybrid general formula 5.

21 Claims, 1 Drawing Sheet

| 5 | R | n |
|---|---|---|
| a | H | 1 |
| b | H | 2 |
| c | H | 3 |
| d | Cl | 1 |
| e | Cl | 2 |
| f | Cl | 3 |
| g | F | 1 |
| h | F | 2 |
| i | F | 3 |
| j | $CH_3$ | 1 |
| k | $CH_3$ | 2 |
| l | $CH_3$ | 3 |

PYRROLO[2,1-C][1,4]BENZODIAZEPINE HYBRIDS AND A PROCESS FOR THE PREPARATION THEREOF

CROSS REFERENCE TO RELATED APPLICATION

This application is a utility application and claims the benefit under 35 USC § 119(a) of India Application No. 1822/DEL/2006 filed Aug. 14, 2006. This disclosure of the prior application is considered part of and is incorporated by reference in the disclosure of this application.

BACKGROUND OF THE INVENTION

1. Field of the Invention

The present invention relates to quinazolinone linked pyrrolo[2,1-c][1,4]benzodiazepine hybrids of general formula 5, useful as potential anti tumour agents and a process for the preparation thereof. Particularly it relates to a process for the preparation of 7-methoxy-8-[n-(6-chloro-2-oxo-4-phenyl-1,2-dihydro-1-quinazolinyl)alkyloxy]-(11aS)-1,2,3,11a-tetrahydro-5H-pyrrolo[2,1-c][1,4]benzodiazepine-5-one with aliphatic chain length variations for these compounds. The structural formula of these novel quinazolinone linked pyrrolo[2,1-c][1,4]benzodiazepines is given below.

formula 5

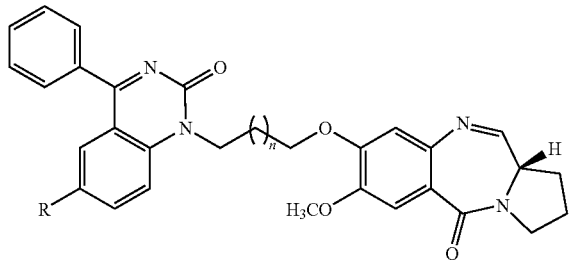

wherein, R is an alkyl or halo group selected from H, Cl, F and $CH_3$ and n=1, 2 or 3.

2. Background Information

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665.; Kohn, K. W. and Speous, C. L. *J. Mol. Biol.*, 1970, 51, 551.; Hurley, L. H.; Gairpla, C. and Zmijewski, M. *Biochem. Biophys. Acta.*, 1977, 475, 521.; Kaplan, D. J. and Hurley, L. H. *Biochemistry*, 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S. and Hurley, L. H. *J. Org. Chem.* 1996, 61, 8141).

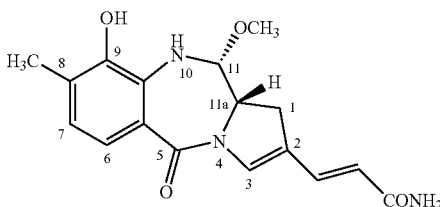

anthramycin

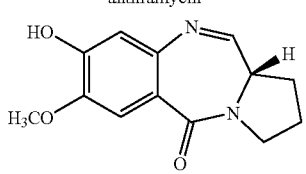

DC-81

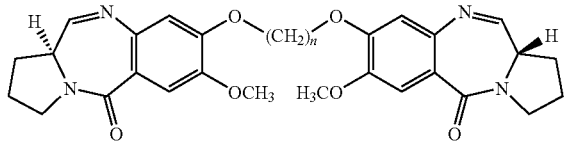

DC-81 dimers (n = 3-5); DSB-120 (n = 3)

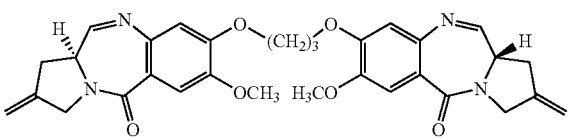

SJG-136

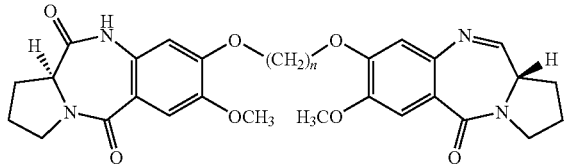

imine-amide PBD dimers; n = 3-5

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). Recently, a non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679).

Naturally occurring pyrrolo[2,1-c][1,4]benzodiazepines belong to a group of antitumour antibiotics derived from *Streptomyces* species. Recently, there is much impetus for the PBD systems as they can recognize and bind to specific sequence of DNA. Examples of naturally occurring PBDs include anthramycin, DC-81, tomaymycin, sibiromycin and neothramycin.

However, the clinical efficacy for these antibiotics is hindered by several limitations, such as poor water solubility, cardiotoxicity, development of drug resistance and metabolic inactivation.

OBJECTIVES OF THE INVENTION

The main objective of the present invention is to provide novel quinazolinone linked pyrrolo[2,1-c][1,4]benzodiazepine hybrids, useful as antitumour agents.

Another objective of this invention is to provide a process for the preparation of novel quinazolinone linked pyrrolo[2,1-c][1,4]benzodiazepine hybrid of formula 5.

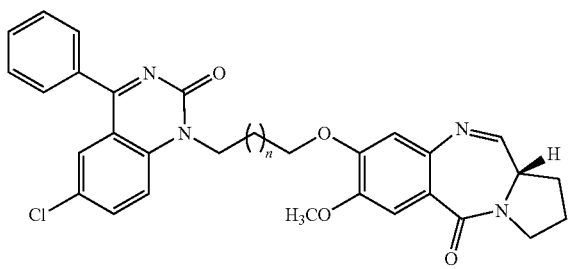

SUMMARY OF THE INVENTION

Accordingly the present invention provides novel quinazolinone linked pyrrolo [2,1-c][1,4]benzodiazepine hybrid of general formula 5, Formula 5

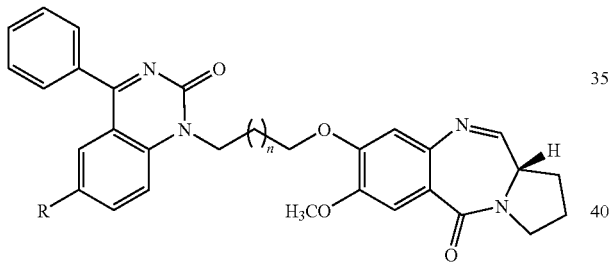

wherein, R is an alkyl or halo group selected from H, Cl, F and $CH_3$ and n=1, 2, 3 or 4.

In an embodiment of the present invention the quinazolinone linked pyrrolo [2,1-c][1,4]benzodiazepine hybrid of formula 5 is represented by the group of the following compounds:

7-Methoxy-8-[3-(6-H-2-oxo-4-phenyl-1,2-dihydro-1-quinazolinyl)propoxy]-(11aS)-1,2,3,11a-tetrahydro-5H-pyrrolo[2,1-c][1,4]benzodiazepine-5-one (5a);

7-Methoxy-8-[4-(6-H-2-oxo-4-phenyl-1,2-dihydro-1-quinazolinyl)butyloxy]-(11aS)-1,2,3,11a-tetrahydro-5H-pyrrolo[2,1-c][1,4]benzodiazepine-5-one (5b);

7-Methoxy-8-[5-(6-H-2-oxo-4-phenyl-1,2-dihydro-1-quinazolinyl)pentyl oxy]-(11aS)-1,2,3,11a-tetrahydro-5H-pyrrolo[2,1-c][1,4]benzodiazepine-5-one (5c);

7-Methoxy-8-[3-(6-chloro-2-oxo-4-phenyl-1,2-dihydro-1-quinazolinyl)propoxy]-(11aS)-1,2,3,11a-tetrahydro-5H-pyrrolo[2,1-c][1,4]benzodiazepine-5-one (5d);

7-Methoxy-8-[4-(6-chloro-2-oxo-4-phenyl-1,2-dihydro-1-quinazolinyl)butyloxy]-(11aS)-1,2,3,11a-tetrahydro-5H-pyrrolo[2,1-c][1,4]benzodiazepine-5-one (5e);

7-Methoxy-8-[5-(6-chloro-2-oxo-4-phenyl-1,2-dihydro-1-quinazolinyl)pentyl oxy]-(11aS)-1,2,3,11a-tetrahydro-5H-pyrrolo[2,1-c][1,4]benzodiazepine-5-one (5f);

7-Methoxy-8-[3-(6-floro-2-oxo-4-phenyl-1,2-dihydro-1-quinazolinyl)propoxy]-(11aS)-1,2,3,11a-tetrahydro-5H-pyrrolo[2,1-c][1,4]benzodiazepine-5-one (5g);

7-Methoxy-8-[4-(6-floro-2-oxo-4-phenyl-1,2-dihydro-1-quinazolinyl)butyloxy]-(11aS)-1,2,3,11a-tetrahydro-5H-pyrrolo[2,1-c][1,4]benzodiazepine-5-one (5h);

7-Methoxy-8-[5-(6-floro-2-oxo-4-phenyl-1,2-dihydro-1-quinazolinyl)pentyl oxy]-(11aS)-1,2,3,11a-tetrahydro-5H-pyrrolo[2,1-c][1,4]benzodiazepine-5-one (5i);

7-Methoxy-8-[3-(6-methyl-2-oxo-4-phenyl-1,2-dihydro-1-quinazolinyl)propoxy]-(11aS)-1,2,3,11a-tetrahydro-5H-pyrrolo[2,1-c][1,4]benzodiazepine-5-one (5j);

7-Methoxy-8-[4-(6-methyl-2-oxo-4-phenyl-1,2-dihydro-1-quinazolinyl)butyloxy]-(11aS)-1,2,3,11a-tetrahydro-5H-pyrrolo[2,1-c][1,4]benzodiazepine-5-one (5k); and 7-Methoxy-8-[5-(6-methyl-2-oxo-4-phenyl-1,2-dihydro-1-quinazolinyl)pentyl oxy]-(11aS)-1,2,3,11a-tetrahydro-5H-pyrrolo[2,1-c][1,4]benzodiazepine-5-one(5l).

In yet another embodiment the structural formula of the representative compounds of quinazolinone linked pyrrolo [2,1-c][1,4]benzodiazepine hybrid of formula 5 are:

5a-c

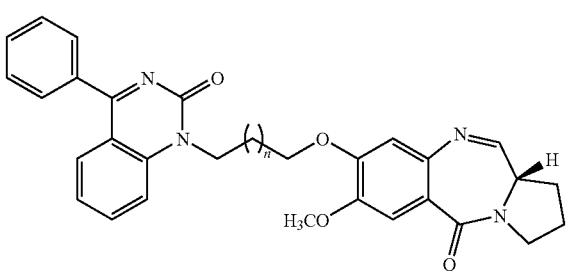

5d-f

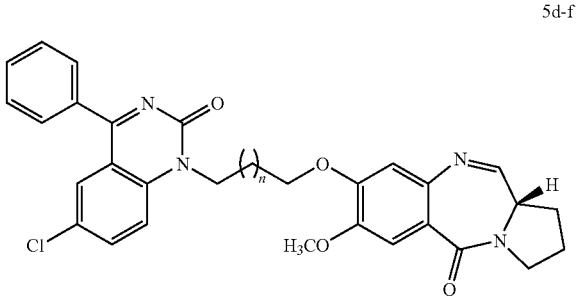

5g-i

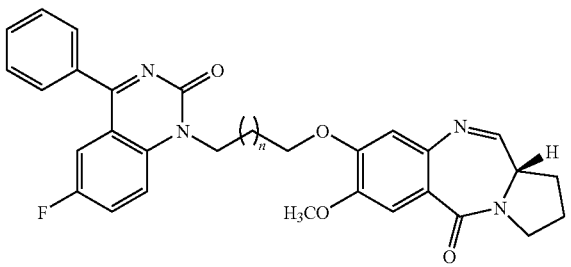

-continued 5j-1

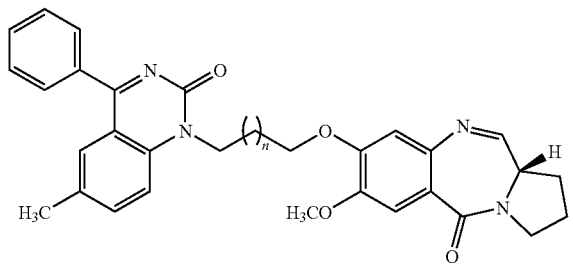

In yet another embodiment quinazolinone linked pyrrolo[2,1-c][1,4]benzodiazepine hybrid of formula 5, exhibits an in vitro anticancer/antitumour activity against human cancer cell lines selected from the group consisting of lung, cervix, breast, colon, prostate and oral cell lines.

In yet another embodiment the concentration of quinazolinone linked pyrrolo[2,1-c][1,4]benzodiazepine hybrid of formula 5 used for in vitro activity against Colo205 for IC50 is in the range of 8 to 15 μm, at an exposure period of at least 48 hrs.

In yet another embodiment the concentration of quinazolinone linked pyrrolo[2,1-c][1,4]benzodiazepine hybrid of formula 5 used for in vitro activity against DU145 for IC50 is in the range of 8 to 15 μm, at an exposure period of at least 48 hrs.

In yet another embodiment the concentration of quinazolinone linked pyrrolo[2,1-c][1,4]benzodiazepine hybrid of formula 5 used for in vitro activity against DWD for IC50 is in the range of 8 to 10 μm, at an exposure period of at least 48 hrs.

In yet another embodiment the concentration of quinazolinone linked pyrrolo[2,1-c][1,4]benzodiazepine hybrid of formula 5 used for in vitro activity against HoP62 for IC50 is 5 μm, at an exposure period of at least 48 hrs.

In yet another embodiment the concentration of quinazolinone linked pyrrolo[2,1-c][1,4]benzodiazepine hybrid of formula 5 used for in vitro activity against HT1080 for IC50 is in the range of 8 to 9 μm, at an exposure period of at least 48 hrs.

In yet another embodiment the concentration of quinazolinone linked pyrrolo[2,1-c][1,4]benzodiazepine hybrid of formula 5 used for in vitro activity against MCF7 for IC50 is in the range of 8 to 12 μm, at an exposure period of at least 48 hrs.

In yet another embodiment the concentration of quinazolinone linked pyrrolo[2,1-c][1,4]benzodiazepine hybrid of formula 5 used for in vitro activity against PC3 for IC50 is in the range of 7 to 11 μm, at an exposure period of at least 48 hrs.

In yet another embodiment the concentration of quinazolinone linked pyrrolo[2,1-c][1,4]benzodiazepine hybrid of formula 5 used for in vitro activity against SiHa for IC50 is in the range of 8 to 15 μm, at an exposure period of at least 48 hrs.

In yet another embodiment the concentration of quinazolinone linked pyrrolo[2,1-c][1,4]benzodiazepine hybrid of formula 5 used for in vitro activity against Zr-75-1 for IC50 is in the range of 8 to 15 μm, at an exposure period of at least 48 hrs.

The present invention further provides a pharmaceutical composition comprising quinazolinone linked pyrrolo[2,1-c][1,4]benzodiazepine hybrid of formula 5, its derivatives, analogues, salts or mixture thereof, optionally with pharmaceutically acceptable carriers, adjuvants and additives.

In an embodiment of the present invention the quinazolinone linked pyrrolo[2,1-c][1,4]benzodiazepine hybrid used in pharmaceutical composition is represented by a general formula 5, Formula 5

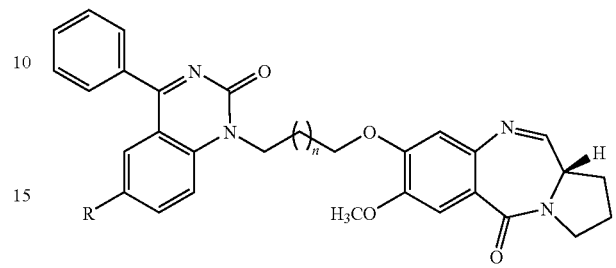

wherein, R is alkyl or halo group selected from H, Cl, F and CH₃ and n=1, 2 or 3.

The present invention further provides a process for the preparation of quinazolinone linked pyrrolo[2,1-c][1,4]benzodiazepine hybrid of formula 5,

5

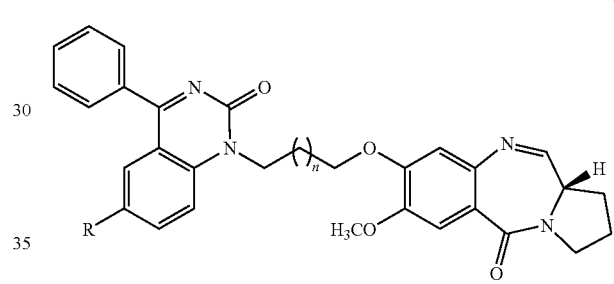

wherein, R is alkyl or halo group selected from H, Cl, F and CH₃ and n=1, 2 or 3, the said process comprising the steps of:
a) reacting (2S)-N-(4-hydroxy-3-methoxy-2-nitrobenzoyl) pyrrolidine-2-carboxaldehyde diethyl thioacetal of formula 2

2

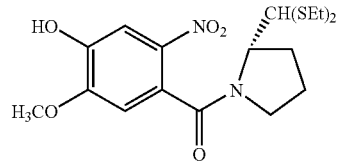

with 1-(n-bromo alkyl)-6-R-4-phenyl-1,2-dihydro-2-quinazolinone of formula 1, wherein R is selected from the group consisting of H, Cl, F and CH₃ and n=1, 2 or 3, in an aprotic water miscible organic solvent,

1

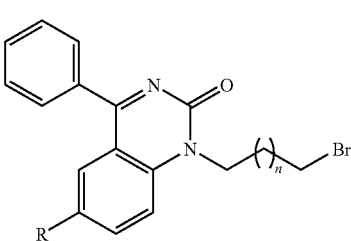

in the presence of anhydrous mild inorganic base, under refluxing temperature in an oil bath, for a period of about 48 hrs, followed by the removal of inorganic base by filtration and evaporating the organic solvent to obtain the resultant crude product and purifying it by known method to obtain the desired product of 2S-N-{4-[3-(6-R-4-phenyl-1,2-dihydro-2-quinazolinone)]alkyl]oxy-5-methoxy-2-nitrobenzoyl}pyrrolidine-2-carboxaldehyde diethylthioacetal of formula 3,

3

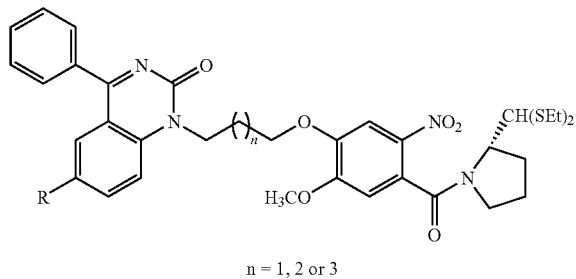

n = 1, 2 or 3 b) reducing 2S-N-{4-[3-(6-R-4-phenyl-1,2-dihydro-2-quinazolinone)]alkyl]oxy-5-methoxy-2-nitrobenzoyl}pyrrolidine-2-carboxaldehyde diethyl thioacetal of formula 3 with anhydrous tin chloride, in an alcohol, under reflux, followed by the evaporation of alcohol and adjusting the pH of the resultant product layer to about 8 by using a base, followed by extraction with ethyl acetate and washing the combined organic phase with brine solution and evaporating the solvent to obtain the desired 2S-N-{4-[3-(6-chloro-4-phenyl-1,2-dihydro-2-quinazolinone)]alkyl]oxy-5-methoxy-2-aminobenzoyl}pyrrolidine-2-carboxaldehyde diethyl thioacetal of formula formula 4, wherein R is selected from the group consisting of H, Cl, F and $CH_3$ and n=1, 2 or 3,

4

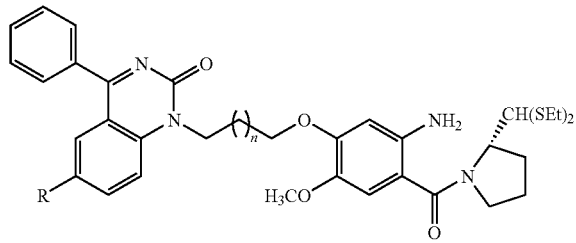

c) reacting 2S-N-{4-[3-(6-chloro-4-phenyl-1,2-dihydro-2-quinazolinone)]alkyl]oxy-5-methoxy-2-aminobenzoyl}pyrrolidine-2-carboxaldehyde diethylthioacetal of formula 4 with mercurous chloride, in a mixture of water and organic solvent, in the presence of mild inorganic, under stirring, at a temperature of about 20-30° C., for a period of 8-12 hrs, followed by the extraction of yellow organic supernatant and washing with sodium bi carbonate and brine, respectively, and evaporating the organic layer, under reduced pressure to obtain the desired product of formula 5.

In yet another embodiment the mild inorganic base used in steps (a) & (b) is potassium carbonate.

In yet another embodiment the aprotic organic solvent used in step (a) is acetone.

In yet another embodiment the organic solvent used in step (c) is acetonitrile.

In yet another embodiment the alcohol used in step (b) is selected from methanol and ethanol.

In yet another embodiment the compounds of formula 5 obtained are represented by a group of the following compounds:

7-Methoxy-8-[3-(6-H-2-oxo-4-phenyl-1,2-dihydro-1-quinazolinyl)propoxy]-(11aS)-1,2,3,11a-tetrahydro-5H-pyrrolo[2,1-c][1,4]benzodiazepine-5-one (5a);

7-Methoxy-8-[4-(6-H-2-oxo-4-phenyl-1,2-dihydro-1-quinazolinyl)butyloxy]-(11aS)-1,2,3,11a-tetrahydro-5H-pyrrolo[2,1-c][1,4]benzodiazepine-5-one (5b);

7-Methoxy-8-[5-(6-H-2-oxo-4-phenyl-1,2-dihydro-1-quinazolinyl)pentyl oxy]-(11aS)-1,2,3,11a-tetrahydro-5H-pyrrolo[2,1-c][1,4]benzodiazepine-5-one (5c);

7-Methoxy-8-[3-(6-chloro-2-oxo-4-phenyl-1,2-dihydro-1-quinazolinyl)propoxy]-(11aS)-1,2,3,11a-tetrahydro-5H-pyrrolo[2,1-c][1,4]benzodiazepine-5-one (5d);

7-Methoxy-8-[4-(6-chloro-2-oxo-4-phenyl-1,2-dihydro-1-quinazolinyl)butyloxy]-(11aS)-1,2,3,11a-tetrahydro-5H-pyrrolo[2,1-c][1,4]benzodiazepine-5-one (5e);

7-Methoxy-8-[5-(6-chloro-2-oxo-4-phenyl-1,2-dihydro-1-quinazolinyl)pentyl oxy]-(11aS)-1,2,3,11a-tetrahydro-5H-pyrrolo [2,1-c][1,4]benzodiazepine-5-one (5f);

7-Methoxy-8-[3-(6-floro-2-oxo-4-phenyl-1,2-dihydro-1-quinazolinyl)propoxy]-(11aS)-1,2,3,11a-tetrahydro-5H-pyrrolo[2,1-c][1,4]benzodiazepine-5-one (5g);

7-Methoxy-8-[4-(6-floro-2-oxo-4-phenyl-1,2-dihydro-1-quinazolinyl)butyloxy]-(11aS)-1,2,3,11a-tetrahydro-5H-pyrrolo[2,1-c][1,4]benzodiazepine-5-one (5h);

7-Methoxy-8-[5-(6-floro-2-oxo-4-phenyl-1,2-dihydro-1-quinazolinyl)pentyl oxy]-(11aS)-1,2,3,11a-tetrahydro-5H-pyrrolo [2,1-c][1,4]benzodiazepine-5-one (5i), 7-Methoxy-8-[3-(6-methyl-2-oxo-4-phenyl-1,2-dihydro-1-quinazolinyl)propoxy]-(11aS)-1,2,3,11a-tetrahydro-5H-pyrrolo[2,1-c][1,4]benzodiazepine-5-one (5j);

7-Methoxy-8-[4-(6-methyl-2-oxo-4-phenyl-1,2-dihydro-1-quinazolinyl)butyloxy]-(11aS)-1,2,3,11a-tetrahydro-5H-pyrrolo[2,1-c][1,4]benzodiazepine-5-one (5k); and 7-Methoxy-8-[5-(6-methyl-2-oxo-4-phenyl-1,2-dihydro-1-quinazolinyl)pentyl oxy]-(11aS)-1,2,3,11a-tetrahydro-5H-pyrrolo[2,1-c][1,4]benzodiazepine-5-one (5l).

In still another embodiment quinazolinone linked pyrrolo [2,1-c][1,4]benzodiazepine hybrid of formula 5a-1 exhibits an in vitro anticancer/antitumour activity against human cancer cell lines selected from the group consisting of lung, cervix, breast, colon, prostate and oral cell lines.

DETAILED DESCRIPTION OF THE INVENTION

Figure 1:
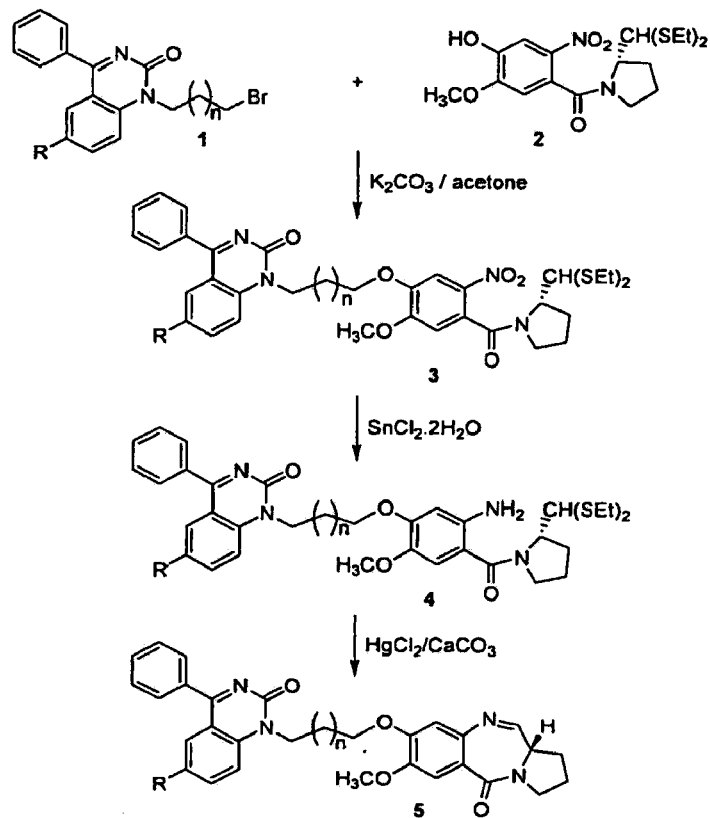
FIG. 1 shows the synthesis of new analogues of pyrrolo[2,1-c][1,4]benzodiazepine hybrids linked at the C-8 position.

The present invention relates to a process for preparation of pyrrolo[2,1-c][1,4]benzodiazepine hybrids of formula 5 of the drawing accompanying the specification where n=1-3 which comprises reacting 1-(n-bromoalkyl)-6-chloro-4-phenyl-1,2-dihydro-2-quinazolinone of formula 1 with 2S-N-(4-hydroxy-5-methoxy-2-nitrobenzoyl)pyrrolidine-2-carboxaldehyde diethyl thioacetal of formula 2 in presence of CH₃COCH₃/K₂CO₃ in a period of 48 h isolating (2S)-N-{4-[5-(6-chloro-4-phenyl-1,2-dihydro-2-quinazolinone)]pentyl]oxy-5-methoxy-2-nitrobenzoyl}pyrrolidine-2-carboxaldehyde diethyl thioacetal of formula 3 by conventional methods, reducing the above nitro compounds of formula 3 with $SnCl_2.2H_2O$ in presence of organic solvent up to a reflux temperature, isolating the (2S)-N-{4-[5-(6-chloro-4-phenyl-1,2-dihydro-2-quinazolinone)]pentyl]oxy-5-methoxy-2-aminobenzoyl}pyrrolidine-2-carboxaldehyde diethyl thioacetal 4 respectively by known methods, reacting the above said amino compound of formula 4 with known deprotecting agents in a conventional manner to give novel pyrrolo[2,1-c][1,4]benzodiazepine hybrids of formula 5, where 'n' are as stated above.

The precursors, 1-(n-bromoalkyl)-6-chloro-4-phenyl-1,2-dihydro-2-quinazolinone of formula 1 (Kamal, A.; Rao, K. R.; Sattur, P. B. *Syn. Commun.* 1980, 10, 799-804) and 2S-N-(4-hydroxy-5-methoxy-2-nitrobenzoyl)pyrrolidine-2-carboxaldehyde diethylthioacetal of formula 2 (Thurston, D. E.; Morris, S. J.; Hartley, J. A. *Chem. Commun.* 1996, 563-565) have been prepared by literature methods.

Some representative compounds of formula 5 for the present invention are given below:

7-Methoxy-8-[3-(6-chloro-2-oxo-4-phenyl-1,2-dihydro-1-quinazolinyl)propoxy]-(11aS)-1,2,3,11a-tetrahydro-5H-pyrrolo[2,1-c][1,4]benzodiazepine-5-one.

7-Methoxy-8-[4-(6-chloro-2-oxo-4-phenyl-1,2-dihydro-1-quinazolinyl)butyloxy]-(11aS)-1,2,3,11a-tetrahydro-5H-pyrrolo[2,1-c][1,4]benzodiazepine-5-one.

7-Methoxy-8-[5-(6-chloro-2-oxo-4-phenyl-1,2-dihydro-1-quinazolinyl)pentyl oxy]-(11aS)-1,2,3,11a-tetrahydro-5H-pyrrolo[2,1-c][1,4]benzodiazepine-5-one.

These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. This resulted in design and synthesis of new congeners as illustrated in FIG. 1, which comprise: 1. The ether linkage at C-8 position of DC-81 intermediates with 1 -(n-bromoalkyl)-6-chloro-4-phenyl-1,2-dihydro-2-quinazolinone moiety. 2. Refluxing the reaction mixtures for 48 h. 3. Synthesis of C-8 linked PBD antitumour antibiotic hybrid imines. 4. Purification by column chromatography using different solvents like ethyl acetate, hexane, dichloromethane and methanol.

The following examples are given by way of illustration and therefore should not be construed to the present limit of the scope of invention.

EXAMPLE 1

To a solution of (2S)-N-(4-hydroxy-3-methoxy-2-nitrobenzoyl)pyrrolidine-2-carboxaldehyde diethyl thioacetal 2 (530 mg, 1.33 mmol) in dry acetone (20 mL) was added anhydrous potassium carbonate (915 mg, 6.65 mmol) and 1-(3-bromopropyl)-6-chloro-4-phenyl-1,2-dihydro-2-quinazolinone 1 (500 mg, 1.33 mmol). The reaction mixture was refluxed in an oil bath for 48 hr. and the reaction was monitored by Thin Layer Chromatography (TLC) using ethyl acetate:hexane (4:6) as a solvent system. The potassium carbonate was then removed by suction filtration and the solvent was evaporated under vacuum to afford the crude product. This was further purified by column chromatography using ethyl acetate:hexane (3:7) as a solvent system to obtain the pure product 3 (738 mg, 80% yield).

$^1$H NMR (CDCl₃) δ1.16-1.34 (m, 6H), 1.58-2.14 (m, 6H), 2.28-2.41 (m, 3H), 2.60-2.93 (m, 4H), 3.14-3.28 (m, 2H), 3.98 (s, 3H), 4.17-4.21 (t, 2H), 4.48-4.50 (m, 1H), 6.78 (s, 1H), 7.38 (s, 1H), 7.55-7.65 (m, 3H), 7.72-7.78 (m, 3H), 7.82-7.84 (m, 2H). FABMS: 697 (M+H)

2S-N-{4-[3-(6-Chloro-4-phenyl-1,2-dihydro-2-quinazolinone)]propyl]oxy-5-methoxy-2-nitrobenzoyl}pyrrolidine-2-carboxaldehyde diethyl thioacetal of formula 3 (500 mg, 0.72 mmol) was dissolved in methanol (10 mL), $SnCl_2.2H_2O$ (880 mg, 3.6 mmol) was added and refluxed until the TLC indicated the completion of the reaction. The methanol was evaporated by vacuum and the aqueous layer was then adjusted to pH 8 with 10% NaHCO₃ solution and extracted with ethyl acetate (2×30 mL). The combined organic phase was dried over Na₂SO₄ and evaporated under vacuum to afford the crude amino diethylthioacetal 4 (450 mg, 95% yield), which was directly used in the next step.

A solution of 2S-N-{4-[3-(6-chloro-4-phenyl-1,2-dihydro-2-quinazolinone)]propyl]oxy-5-methoxy-2-aminobenzoyl}pyrrolidine-2-carboxaldehyde diethyl thioacetal 4 (666 mg, 1 mmol), HgCl₂ (613 mg, 2.26 mmol) and CaCO₃ (240 mg, 2.46 mmol) in acetonitrile-water (4:1) was stirred slowly at room temperature for overnight until complete loss of starting material as indicated by the TLC. The clear yellow organic supernatant was extracted with ethyl acetate and washed with saturated 5% NaHCO₃ (20 mL), brine (20 mL) and the combined organic phase was dried over Na₂SO₄. The organic layer was evaporated in vacuum to afford a white solid, which was first eluted on a column chromatography with ethyl acetate to remove mercuric salts, and then with dichloromethane:methanol (9:1) to obtain the pure product 5d (326 mg, 60% yield).

$^1$H NMR (CDCl₃) δ 1.85-2.26 (m, 6H), 2.33-2.46 (m, 4H), 3.52-3.93 (m, 1H), 3.98 (s, 3H), 4.11-4.25 (m, 2H), 6.96 (s, 1H), 7.31-7.42 (m, 1H), 7.53-7.61 (m, 3H), 7.68-7.76 (m, 3H), 7.81-7.84 (m, 2H), 7.94 (d, 1H, J=5.2 Hz). FABMS: 543 (M+H)

EXAMPLE 2

To a solution of (2S)-N-(4-hydroxy-3-methoxy-2-nitrobenzoyl)pyrrolidine-2-carboxaldehyde diethyl thioacetal 2 (512 mg, 1.28 mmol) in dry acetone (20 mL) was added anhydrous potassium carbonate (880 mg, 6.40 mmol) and 1-(4-bromobutyl)-6-chloro-4-phenyl-1,2-dihydro-2-quinazolinone 1 (500 mg, 1.28 mmol). The reaction mixture was refluxed in an oil bath for 48 hr. and the reaction was monitored by Thin Layer Chromatography (TLC) using ethyl acetate:hexane (2:8) as a solvent system. The potassium carbonate was then removed by suction filtration and the solvent was evaporated under vacuum to afford the crude product. This was further purified by column chromatography using ethyl acetate:hexane (3:7) as a solvent system to obtain the pure product 3 (605 mg, 82% yield).

$^1$H NMR (CDCl₃) δ1.18-1.38 (m, 8H), 1.59-2.18 (m, 6H), 2.26-2.42 (m, 3H), 2.53-2.90 (m, 4H), 3.18-3.29 (m, 2H), 3.96 (s, 3H), 4.18 (t, 2H), 4.54-4.55 (m, 1H), 6.73 (s, 1H), 7.4 (s, 1H), 7.6-7.68 (m, 3H), 7.75-7.85 (m, 3H), 7.98-8.0 (m, 2H). FABMS: 711 (M+H)

2S-N-{4-[4-(6-Chloro-4-phenyl-1,2-dihydro-2-quinazolinone)]butyl]oxy-5-methoxy-2-nitrobenzoyl}pyrrolidine-2-carboxaldehyde diethyl thioacetal of formula 3 (500 mg, 0.7 mmol) was dissolved in methanol (10 mL), $SnCl_2.2H_2O$ (798 mg, 3.5 mmol) was added and refluxed until the TLC indicated the completion of the reaction. The methanol was evaporated by vacuum and the aqueous layer was then adjusted to pH 8 with 10% NaHCO₃ solution and extracted with ethyl acetate (2×30 mL). The combined organic phase was dried over $Na_2SO_4$ and evaporated under vacuum to afford the crude amino diethylthioacetal 4 (355 mg, 95% yield), which was directly used in the next step.

A solution of 2S-N-{4-[4-(6-chloro-4-phenyl-1,2-dihydro-2-quinazolinone)]butyl]oxy-5-methoxy-2-aminobenzoyl}pyrrolidine-2-carboxaldehyde diethyl thioacetal 4 (680 mg, 1 mmol), $HgCl_2$ (613 mg, 2.26 mmol) and $CaCO_3$ (240 mg, 2.46 mmol) in acetonitrile:water (4:1) was stirred slowly at room temperature for overnight until complete loss of starting material as indicated by the TLC. The clear yellow organic supernatant was extracted with saturated 5% $NaHCO_3$ (20 mL), brine (20 mL) and the combined organic phase was dried over $Na_2SO_4$. The organic layer was evaporated in vacuum to afford a white solid, which was first eluted on a column chromatography with ethyl acetate to remove mercuric salts, and then with dichloromethane:methanol (9:1) to obtain the pure product 5e (306 mg, 55% yield).

$^1$H NMR ($CDCl_3$) δ1.81-2.25 (m, 8H), 2.3-2.4 (m, 4H), 3.5-3.9 (m, 1H), 3.95 (s, 3H), 4.10-4.20 (m, 2H), 6.90 (s, 1H), 7.30-7.40 (m, 1H), 7.51-7.60 (m, 3H), 7.65-7.75 (m, 3H), 7.78-7.81 (m, 2H), 7.91 (d, 1H, J=5.2 Hz). FABMS: 557 (M+H)

EXAMPLE 3

To a solution of (2S)-N-(4-hydroxy)-3-methoxy-2-nitrobenzoyl)pyrrolidine-2-carboxaldehyde diethyl thioacetal 2 (400 mg, 1 mmol) in dry acetone (20 mL) was added anhydrous potassium carbonate (690 mg, 5 mmol) and 1-(5-bromopentyl)-6-chloro-4-phenyl-1,2-dihydro-2-quinazolinone 1 (405 mg, 1 mmol). The reaction mixture was refluxed in an oil bath for 48 hr and the reaction was monitored by Thin Layer Chromatography (TLC) using ethyl acetate:hexane (4:6) as a solvent system. The potassium carbonate was then removed by suction filtration and the solvent was evaporated under vacuum to afford the crude product. This was further purified by column chromatography using ethylacetate:hexane (3:7) as a solvent system to obtain the pure product 3 (617 mg, 82% yield).

$^1$H NMR ($CDCl_3$) δ1.2-1.4 (m, 8H), 1.6-2.2 (m, 8H), 2.25-2.4 (m, 3H), 2.5-2.9 (m, 4H), 3.2-3.3 (m, 2H), 3.95 (s, 3H), 4.15 (t, 2H), 4.51-4.52 (m, 1H), 6.75 (s, 1H), 7.3 (s, 1H), 7.5-7.6 (m, 3H), 7.65-7.75 (m, 3H), 7.78-7.8 (m, 2H). FABMS: 725 (M+H)

2S-N-{4-[5-(6-Chloro-4-phenyl-1,2-dihydro-2-quinazolinone)]pentyl]oxy-5-methoxy-2-nitrobenzoyl}pyrrolidine-2-carboxaldehyde diethyl thioacetal of formula 3 (500 mg, 0.69 mmol) was dissolved in methanol (10 mL), $SnCl_2.2H_2O$ (786 mg, 3.45 mmol) was added and refluxed until the TLC indicated the completion of the reaction. The methanol was then evaporated in vacuum and the aqueous layer was then adjusted to pH 8 with 10% $NaHCO_3$ solution and extracted with ethyl acetate (60 mL). The combined organic phase was dried over $Na_2SO_4$ and evaporated under vacuum to afford the crude amino diethyl thioacetal 4 (460 mg, 96% yield), which was directly used in the next step.

A solution of 2S-N-{4-[5-(6-chloro-4-phenyl-1,2-dihydro-2-quinazolinone)]pentyl]oxy-5-methoxy-2-aminobenzoyl}pyrrolidine-2-carboxaldehyde diethyl thioacetal 4 (694 mg, 1 mmol), $HgCl_2$ (613 mg, 2.26 mmol) and $CaCO_3$ (240 mg, 2.46 mmol) in acetonitrile-water (4:1) was stirred slowly at room temperature for overnight until complete loss of starting material as indicated by the TLC. The clear yellow organic supernatant was extracted with ethyl acetate and washed with saturated 5% $NaHCO_3$ (20 mL), brine (20 mL) and the combined organic phase was dried over $Na_2SO_4$. The organic layer was evaporated in vacuum and to afford a white solid, which was first eluted on a column chromatography with ethyl acetate to remove mercuric salts, and then with dichloromethane:methanol (9:1) to obtain the pure product 5f (320 mg, 56% yield).

$^1$H NMR ($CDCl_3$) δ 1.73-2.15 (m, 10H), 2.25-2.38 (m, 4H), 3.45-3.87 (m, 1H), 3.93 (s, 3H), 4.05-4.10 (m, 2H), 6.83 (s, 1H), 7.24-7.32 (m, 1H), 7.43-7.58 (m, 3H), 7.63-7.72 (m, 3H), 7.72-7.79 (m, 2H), 7.87 (d, 1H, J=5.2 Hz). FABMS: 571 (M+H)

Cytotoxicity: The compounds 7-methoxy-8-[3-(6-chloro-2-oxo-4-phenyl-1,2-dihydro-1-quinazolinyl)propoxy]-(11aS)-1,2,3,11a-tetrahydro-5H-pyrrolo[2,1-c][1,4]benzodiazepine-5-one and 7-methoxy-8-[5-(6-chloro-2-oxo-4-phenyl-1,2-dihydro-1-quinazolinyl)pentyloxy]-(11aS)-1,2,3,11a-tetrahydro-5H-pyrrolo [2,1-c][1,4]benzodiazepine-5-one were evaluated for in vitro anticancer activity against nine human tumour cells derived from six cancer types (colon, prostate, oral, lung, cervix and breast cancer) as shown in (Table 1).

Compounds 5d and 5f have been evaluated for their in vitro cytotoxicity in selected human cancer cell lines of colon (Colo205), lung (Hop-62), cervix (SiHa), prostate (DU145, PC3), oral (DWD, HT1080), and breast (MCF7, Zr-75-1) origin. A protocol of 48 h continuous drug exposure and an adriamycin (ADR) protein assay has been used to estimate cell viability or growth. The results are expressed as percent of cell growth determined relative to that of untreated control cells (Table 1). Compounds 5d and 5f shows promising cytotoxicity against some cancer cell lines.

TABLE 1

The percentage cell growth data for representative quinazolinone-PBD hybrids

Activity status in terms of $IC_{50}$ values

| Compd | Colo205 Colon | DU145 Prostate | DWD Oral | Hop62 Lung | HT1080 Oral | MCF7 Breast | PC3 Prostate | SiHa Cervix | Zr-75-1 Breast |
|---|---|---|---|---|---|---|---|---|---|
| 5d | 8 | 8 | 5 | 6 | 9 | 12 | 11 | 16 | 8 |
| 5f | 15 | 10 | 5 | 5 | 8 | 8 | 7 | 16 | 8 |
| ADR | 5 | 6 | 2 | 5 | 4 | 5 | 5 | 5 | 5 |

Compounds 5d and 5f exhibited less than 20% cell growth at μg/mL concentration in some cell lines. Compounds 5d and 5f suppress Colo205 cell growth by 92% and 85%, DU145 cell growth by 92% and 90%, DWD cell growth by 95%, Hop62 cell growth by 94% and 95%, HT1080 cell growth by 91% and 92%, MCF7 cell growth by 88% and 92% and PC3 cell growth by 89% and 93%. They are suppressing the SiHa cell growth by 84% and Zr-25-1 cell growth by 92%.

The DNA binding activity for these compounds has been examined by thermal denaturation studies using calf thymus (CT) DNA. Melting studies show that these compounds stabilize the thermal helix→coil or melting stabilization ($\Delta T_m$) for the CT-DNA duplex at pH 7.0, incubated at 37° C., where PBD/DNA molar ratio is 1:5. In this assay these compounds elevate the helix melting temperature of CT-DNA in a range of 1.3-2.3° C. after incubation for 18 h at 37° C.

What is claimed is:

1. A compound having formula 5:

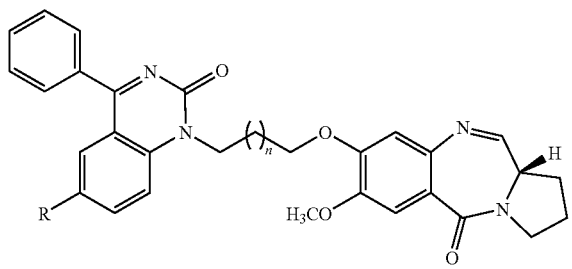

wherein R is selected from the group consisting of H, Cl, F and $CH_3$; and n =1, 2, 3 or 4.

2. The compound according to claim 1 wherein the compound is selected from the group consisting of:

7-Methoxy-8-[3-(6-H-2-oxo-4-phenyl-1,2-dihydro- 1 - quinazolinyl)propoxy]-(11 aS)-1,2,3,11 a-tetrahydro-5H-pyrrolo[2,1-c][1,4]benzodiazepine-5-one (5a);

7-Methoxy-8-[4-(6-H-2-oxo-4-phenyl-1,2-dihydro-1-quinazolinyl)butyloxy]-(11 aS)-1,2,3,11a-tetrahydro-5H-pyrrolo[2,1-c][1,4]benzodiazepine-5-one (5b);

7-Methoxy-8-[5-(6-H-2-oxo-4-phenyl-1,2-dihydro- 1 - quinazolinyl)pentyl oxy]-(11 aS)-1,2,3,11 a-tetrahydro-5H-pyrrolo[2,1-c][1,4]benzodiazepine-5-one (5c);

7-Methoxy-8-[3-(6-chloro-2-oxo-4-phenyl-1,2-dihydro-1 - quinazolinyl)propoxy]-(11 aS)-1,2,3,11a-tetrahydro-5H-pyrrolo[2,1-c][1,4]benzodiazepine-5-one (5d);

7-Methoxy-8-[4-(6-chloro-2-oxo-4-phenyl- 1,2-dihydro-1 -quinazolinyl)butyloxy]-(11 aS)-1,2,3,11a-tetrahydro-5H-pyrrolo[2,1-c][1,4]benzodiazepine-5-one (5e);

7-Methoxy-8-[5-(6-chloro-2-oxo-4-phenyl-1,2-dihydro-1 - quinazolinyl)pentyl oxy]-(11 aS)-1,2,3,11 a-tetrahydro-5H-pyrrolo[2, 1-c][1,4]benzodiazepine-5-one (5f);

7-Methoxy-8-[3-(6-floro-2-oxo-4-phenyl-1,2-dihydro-1 - quinazolinyl)propoxy]-(11 aS)-1,2,3,11 a-tetrahydro-5H-pyrrolo [2,1-c][1,4]benzodiazepine-5-one (5g);

7-Methoxy-8-[4-(6-floro-2-oxo-4-phenyl-1,2-dihydro-1 - quinazolinyl)butyloxy]-(11 aS)-1,2,3,11 a-tetrahydro-5H-pyrrolo[2,1-c][1,4]benzodiazepine-5-one (5h);

7-Methoxy-8-[5-(6-floro-2-oxo-4-phenyl-1,2-dihydro-1-quinazolinyl)pentyl oxy]-(11 aS)-1,2,3,11a-tetrahydro-5H-pyrrolo[2,1-c][1,4]benzodiazepine-5-one (5i);

7-Methoxy-8-[3-(6-methyl-2-oxo-4-phenyl-1,2-dihydro-1-quinazolinyl)propoxy]-(11 aS)-1,2,3,11a-tetrahydro-5H-pyrrolo[2,1-c][1,4]benzodiazepine-5-one (5j);

7-Methoxy-8- [4-(6-methyl-2-oxo-4-phenyl-1,2-dihydro-1-quinazolinyl)butyloxy]-(11 aS)-1,2,3,11a-tetrahydro-5H-pyrrolo[2,1-c][1,4]benzodiazepine-5-one (5k); and 7-Methoxy-8-[5-(6-methyl-2-oxo-4-phenyl-1,2-dihydro-1-quinazolinyl)pentyl oxy]-(11 aS)-1,2,3,11a-tetrahydro-5H-pyrrolo[2,1-c][1,4]benzodiazepine-5-one (5l).

3. The compound according to claim 2, wherein the compound has the structural formula selected from the group consisting of the formulae 5a-c, 5d-f, 5g-i, and 5-j-l:

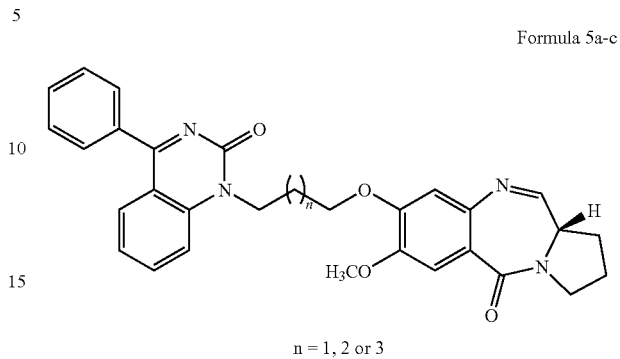

Formula 5a-c n = 1, 2 or 3

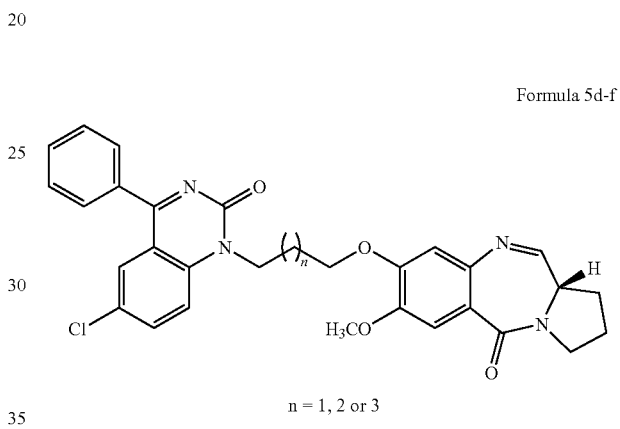

Formula 5d-f n = 1, 2 or 3

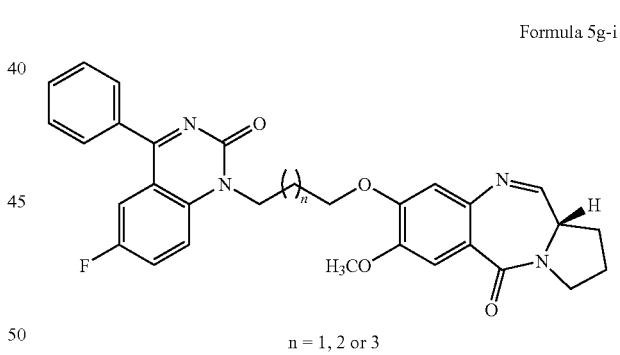

Formula 5g-i n = 1, 2 or 3

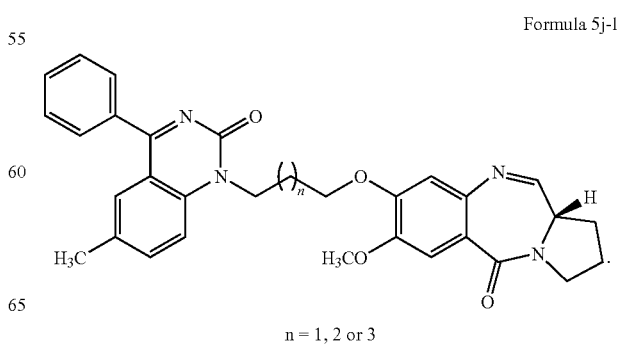

Formula 5j-l n = 1, 2 or 3 with the further proviso that in each of the formulae 5a-c, 5d-f, 5g-i, and 5-j-l, n=1, 2 or 3.

4. A pharmaceutical composition comprising a compound of claim 1, or derivatives, analogues, salts or mixtures thereof, the composition optionally further including pharmaceutically acceptable carriers, adjuvants and/or additives.

5. The pharmaceutical composition according to claim 4, wherein n=1, 2 or 3.

6. A process for the preparation of a compound of formula 5:

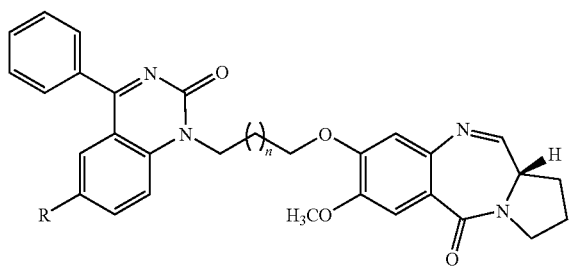

wherein R is selected from the group consisting of H, Cl, F and CH$_3$; and n=1, 2 or 3, said process comprising the steps of:

a) reacting (2S)-N-(4-hydroxy-3-methoxy-2-nitrobenzoyl)pyrrolidine-2-carboxaldehyde diethyl thioacetal of formula 2

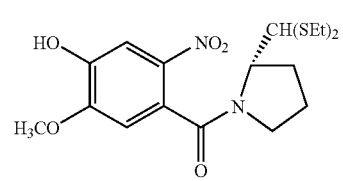

with 1-(3-bromo alkyl)-6-R-4-phenyl-1,2-dihydro-2-quinazolinone of formula 1,

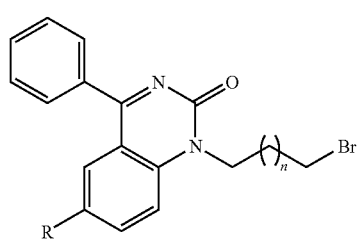

wherein R is selected from the group consisting of H, Cl, F and CH$_3$ and n=1, 2 or 3, in an aprotic water miscible organic solvent, in the presence of anhydrous mild inorganic base, under refluxing temperature in an oil bath, for a period of about 48 hrs, followed by the removal of inorganic base by filtration and evaporating the organic solvent to obtain the resultant crude product and purifying it by known method to obtain the desired product of 2S-N-{4-[3-(6-R-4-phenyl-1,2-dihydro-2-quinazolinone)]alkyl]oxy-5-methoxy-2-nitrobenzoyl}pyrrolidine-2-carboxaldehyde diethyl thioacetal of formula 3, wherein n=1, 2 or 3

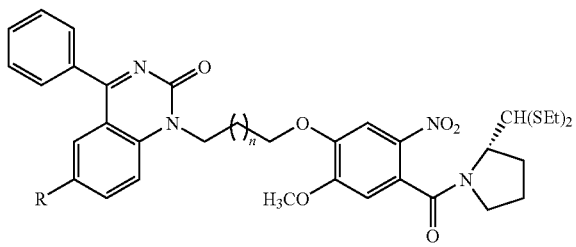

b) reducing 2S-N-{4-[3-(6-R-4-phenyl-1,2-dihydro-2-quinazolinone)]alkyl]oxy-5-methoxy-2-nitrobenzoyl}pyrrolidine-2-carboxaldehyde diethyl thioacetal of formula 3 with anhydrous tin chloride, in an alcohol, under reflux, followed by the evaporation of alcohol and adjusting the pH of the resultant product layer to about 8 by using a base, followed by extraction with ethyl acetate and washing the combined organic phase with brine solution and evaporating the solvent to obtain the desired 2S-N-{4-[3-(6-chloro-4-phenyl-1,2-dihydro-2-quinazolinone)]alkyl]oxy-5-methoxy-2-aminobenzoyl}pyrrolidine-2-carboxaldehyde diethyl thioacetal of formula formula 4, wherein R is selected from the group consisting of H, Cl, F and CH$_3$ and n=1, 2 or 3,

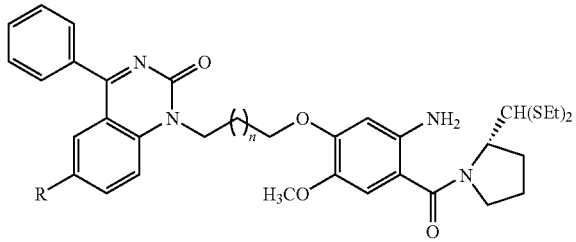

c) reacting 2S-N-{4-[3-(6-chloro-4-phenyl-1,2-dihydro-2-quinazolinone)]alkyl]oxy-5-methoxy-2-aminobenzoyl}pyrrolidine-2-carboxaldehyde diethylthioacetal of formula 4 with mercurous chloride, in a mixture of water and organic solvent, in the presence of mild inorganic, under stirring, at a temperature of about 20-30° C., for a period of 8-12 hrs, followed by the extraction of yellow organic supernatant and washing with sodium bi carbonate and brine, respectively, and evaporating the organic layer, under reduced pressure to obtain the desired product of formula 5.

7. The process according to claim 6, wherein the mild inorganic base used in steps (a) & (b) is potassium carbonate.

8. The process according to claim 6, wherein the aprotic organic solvent used in step (a) is acetone and acetonitrile.

9. The process according to claim 6, wherein the organic solvent used in step (c) is acetonitrile.

10. The A process according to claim 6, wherein the alcohol used in step (b) is selected from methanol and ethanol.

11. The process according to claim 6, wherein the compound of formula 5 obtained thereby is selected from the group consisting of:

7-Methoxy-8-[3-(6-H-2-oxo-4-phenyl-1,2-dihydro-1-quinazolinyl)propoxy]-(11aS)-1,2,3,11a-tetrahydro-5H-pyrrolo[2,1-c][1,4]benzodiazepine-5-one (5a);

7-Methoxy-8-[4-(6-H-2-oxo-4-phenyl-1,2-dihydro-1-quinazolinyl)butyloxy]-(11aS)-1,2,3,11a-tetrahydro-5H-pyrrolo[2, 1-c][1,4]benzodiazepine-5-one (5b);

7-Methoxy-8-[5-(6-H-2-oxo-4-phenyl-1,2-dihydro-1-quinazolinyl)pentyl oxy]-(11aS)-1,2,3,11 a-tetrahydro-51-J-pyrrolo [2,1-c][1,4]benzodiazepine-5-one (5c);

7-Methoxy-8-[3-(6-chloro-2-oxo-4-phenyl-1,2-dihydro-1-quinazolinyl)propoxy]-(11aS)-1,2,3,11a-tetrahydro-5H-pyrrolo[2,1-c][1,4]benzodiazepine-5-one(5d);

7-Methoxy-8-[4-(6-chloro-2-oxo-4-phenyl-1,2-dihydro-1-quinazolinyl)butyloxy]-(11aS)-1,2,3,11a-tetrahydro-5H-pyrrolo[2,1-c][1,4]benzodiazepine-5-one (5e);

7-Methoxy-8-[5-(6-chloro-2-oxo-4-phenyl-1,2-dihydro-1 -quinazolinyl)pentyl oxy]-(11 aS)-1,2,3,11a-tetrahydro-511-pyrrolo [2,1-c][1,4]benzodiazepine-5-one (51f);

7-Methoxy-8-[3-(6-floro-2-oxo-4-phenyl-1,2-dihydro-1-quinazolinyl)propoxy]-(11aS)-1,2,3,11a-tetrahydro-5H-pyrrolo [2,1-c][1,4]benzodiazepine-5-one(5g);

7-Methoxy-8-[4-(6-floro-2-oxo-4-phenyl-1,2-dihydro-1-quinazolinyl)butyloxy]-(11aS)-1,2,3,11a-tetrahydro-5H-pyrrolo [2,1-c][1,4]benzodiazepine-5 -one (5h);

7-Methoxy-8-[5-(6-floro-2-oxo-4-phenyl-1,2-dihydro-1-quinazolinyl)pentyl oxy]-(11aS)-1,2,3,11a-tetrahydro-5H-pyrrolo [2,1-c][1,4]benzodiazepine-5-one (5i);

7-Methoxy-8-[3-(6-methyl-2-oxo-4-phenyl-1,2-dihydro-1-quinazolinyl)propoxy]-(11aS)-1,2,3,11a-tetrahydro-5H-pyrrolo[2, 1-c][1,4]benzodiazepine-5-one (5j);

7-Methoxy-8-[4-(6-methyl-2-oxo-4-phenyl-1,2-dihydro-1-quinazolinyl)butyloxy]-(11aS)-1,2,3,11a-tetrahydro-5H -pyrrolo[2,1-c][1,4]benzodiazepine-5-one (5k) and 7-Methoxy-8-[5-(6-methyl-2-oxo-4-phenyl-1,2-dihydro-1-quinazolinyl)pentyl oxy]-(11 aS)-1,2,3,11a-tetrahydro-5H -pyrrolo [2,1-c][1,4]benzodiazepine-5-one (5l).

12. A method for inhibiting the growth of cancer cells, comprising contacting human cancer cells selected from the group consisting of lung, cervix, breast, colon, prostate and oral cells, with a compound having formula 5:

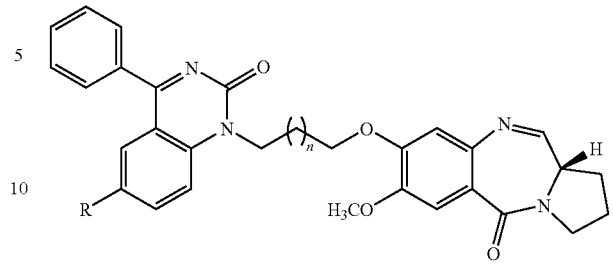

wherein R is selected from the group consisting of H, Cl, F and $CH_3$; and n=1, 2, 3 or 4, and observing the effect of the compound on cell growth.

13. The method according to claim 12, wherein the concentration of the compound used against Colo205 for IC50 is in the range of 8 to 15 μm, at an exposure period of at least 48 hrs.

14. The method according to claim 12, wherein the concentration of the compound used against DU145 for IC50 is in the range of 8 to 15 μm, at an exposure period of at least 48 hrs.

15. The method according to claim 12, wherein the concentration of the compound used against DWD for IC50 is in the range of 8 to 10 μm, at an exposure period of at least 48 hrs.

16. The method according to claim 12, wherein the concentration of the compound used against HoP62 for IC50 is 5 μm, at an exposure period of at least 48 hrs.

17. The method according to claim 12, wherein the concentration of the compound used against HT1080 for IC50 is in the range of 8 to 9 μm, at an exposure period of at least 48 hrs.

18. The method according to claim 12, wherein the concentration of the compound used against MCF7 for IC50 is in the range of 8 to 12 μm, at an exposure period of at least 48 hrs.

19. The method according to claim 12, wherein the concentration of the compound used against PC3 for IC50 is in the range of 7 to 11 μm, at an exposure period of at least 48 hrs.

20. The compound according to claim 12, wherein the concentration of the compound used against SiHa for IC50 is in the range of 8 to 15 μm, at an exposure period of at least 48 hrs.

21. The method according to claim 12, wherein the concentration of the compound used against Zr-75-1 for IC50 is in the range of 8 to 15 μm, at an exposure period of at least 48 hrs.

* * * * *